United States Patent [19]

Des Marais et al.

[11] 4,182,728

[45] Jan. 8, 1980

[54] PRESERVATION OF DICARBOXYLIC ACID CHLORIDES

[75] Inventors: Thomas A. Des Marais, Norwood; Michael K. Hughes, Cincinnati, both of Ohio

[73] Assignee: The Procter & Gamble Company, Cincinnati, Ohio

[21] Appl. No.: 933,317

[22] Filed: Aug. 14, 1978

[51] Int. Cl.$^2$ .................... C07C 51/42; C07C 51/58
[52] U.S. Cl. ................................................ 260/544 Y
[58] Field of Search ................................... 260/544 Y

[56] References Cited

U.S. PATENT DOCUMENTS 1,936,739  11/1933  Townend ..................... 260/544 Y

FOREIGN PATENT DOCUMENTS 49-30311  3/1974  Japan ..................... 260/544 Y Primary Examiner—Norman Morgenstern
Attorney, Agent, or Firm—Jeffrey R. Melnikoff; Fredrick H. Braun; Richard C. Witte

[57] ABSTRACT

Discoloration of dicarboxylic acid chlorides having 4 to 10 carbon atoms, especially those made by reacting the corresponding dicarboxylic acid with phosphorus trichloride, is inhibited by the addition of a dicarboxylic acid thereto. Addition of a dicarboxylic acid to a dicarboxylic acid chloride which has already discolored precipitates impurities and thus clarifies the dicarboxylic acid chloride. The clarified dicarboxylic acid chlorides are useful as starting materials to make polyester foam materials.

14 Claims, No Drawings

PRESERVATION OF DICARBOXYLIC ACID CHLORIDES

TECHNICAL FIELD

The field of invention is the art of handling and stabilizing dicarboxylic acid chlorides which result from the treatment of dicarboxylic acids with phosphorus trichloride. In particular, the invention relates to removing, or preventing the appearance of, discolored products of spontaneous decomposition which are observed in certain untreated dicarboxylic acid chlorides.

BACKGROUND ART

Aliphatic dicarboxylic acid chlorides, especially adipyl chloride, are used as starting materials for the manufacture of certain polyester foam materials, in accordance with the teaching of a U.S. application, Ser. No. 843,606, filed by T. A. DesMarais on Oct. 19, 1977. Specifically, that application (which is hereby incorporated herein by reference) teaches that straight-chain aliphatic compounds having 4 to 10 carbon atoms and acid chloride groups on each terminal end of the aliphatic chain may be combined with a guadrifunctional polyol, a propoxylated pentaerythritol cross linking agent and sodium carbonate to make a resilient polyester foam material which is useful in absorbent products such as catamenial tampons.

A principal method to synthesize the acid chlorides above-described is to react the corresponding carboxylic acid with phosphorus trichloride according to the following reaction:

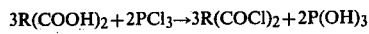

$$3R(COOH)_2 + 2PCl_3 \rightarrow 3R(COCl)_2 + 2P(OH)_3$$

where R is an aliphatic chain. A more complete discussion of this reaction may be found in U.S. Pat. No. 1,936,739, issued to Townend on Nov. 28, 1933, which is hereby incorporated herein by reference. One significant problem with this synthetic route is that the resulting chlorides of dicarboxylic acids have a tendency to discolor upon standing. The reason for this discoloration and the nature of the discoloring material are not known to the inventors hereof, although the discolored matter is believed to be one or more degradation products of the dicarboxylic acid chloride. If discolored diacid chloride is used to make the polyester foam described above, the foam itself will be discolored. Since consumers dislike the resulting discolored foam materials, they are unsuitable for use in consumer products such as a tampon.

The Townend reference is the only prior art of which the inventors are aware. That reference teaches that it is desirable to treat an acid chloride formed by the phosphorus trichloride reaction by bubbling chlorine gas through the reaction mixture with the specific purpose of completing the reaction and eliminating any carboxylic acid residue from the resulting diacid chloride. That reference does not teach any way to prevent the discoloration of the acid chloride resulting from the reaction, and it specifically teaches that it is desirable to eliminate the carboxylic acid starting material from the produce of the reaction.

Accordingly, it is an object of this invention to clarify or to preserve the clarity of an aliphatic dicarboxylic acid chloride, and it is a further object of this invention to produce a dicarboxylic acid chloride starting material which may be used in the manufacture of substantially colorless polyester foams according to the process described in the DesMarais application cited on page 2 hereof.

DISCLOSURE OF INVENTION

A dicarboxylic acid chloride, selected from a group consisting of: succinyl chloride, glutaryl chloride, adipyl chloride, pimelyl chloride, suberyl chloride, azelayl chloride, and sebacyl chloride, is clarified or preserved by contacting therewith a minor amount of a dicarboxylic acid selected from a group consisting of: succinic acid, glutaric acid, adipic acid, pimelic acid, suberic acid, azelaic acid, or sebacic acid. The dicarboxylic acid selected may be the same as or different from the dicarboxylic acid analog of the chloride being clarified or preserved. The lower limit of presence of the dicarboxylic acid as a preservative is roughly 2% by weight of the composition. There is no fixed maximum quantity of the dicarboxylic acid which may be present in practicing the invention, except that it is undesirable to add so much of the selected dicarboxylic acid (which is a solid at room temperature) to the selected diacid chloride (which is a liquid at room temperature) that the latter component is entrained in an excess of preservative. As a consequence, a preferred composition will contain less than about 20% (by weight of the composition) of a dicarboxylic acid, although the invention is operable if even 90% by weight of the composition consists of a dicarboxylic acid. The most preferred upper limit of acid present will not exceed about 5% by weight of the composition.

Instead of placing a quantity of dicarboxylic acid directly in contact with the diacid chloride, it is also possible to accomplish the same result by adding a minor amount of water (i.e., about 0.5% to 1% by weight of the chloride) to the diacid chloride, which results in the generation of a small amount of the dicarboxylic acid analog of the diacid chloride. This is a less preferred manner of practicing the invention because the diacid chlorides are more expensive than the corresponding diacid, so generation of an inexpensive preservative from the more expensive preserved compound is economically unsound at present.

Detailed Description of the Invention

While this specification concludes with claims particularly pointing out and distinctly claiming the subject matter the inventors consider to be their invention, it is believed that the invention disclosed herein can be better understood from the following detailed description.

First, Table 1 is incorporated in this specification as an aid to the reader, and lists dicarboxylic acids and diacid chlorides according to the chemical formulas, the strict nomenclature names, and the common names thereof.

TABLE 1

| Formula* | IUPAC** and Common Names | Chloride |
| --- | --- | --- |
| $X_2$ | ethanedioic (oxalic) acid | oxalyl chloride |
| $X-CH_2-X$ | propanedioic (malonic) acid | malonyl chloride |
| $X-(CH_2)_2-X$ | butanedioic (succinic) acid | succinyl chloride |
| $X-(CH_2)_3-X$ | pentanedioic (glutaric) acid | glutaryl chloride |
| $X-(CH_2)_4-X$ | hexanedioic (adipic) acid | adipyl chloride |
| $X-(CH_2)_5-X$ | heptanedioic (pimelic) acid | pimelyl chloride |
| $X-(CH_2)_6-X$ | octanedioic (suberic) acid | suberyl chloride |
| $X-(CH_2)_7-X$ | nonanedioic (azelaic) acid | azelayl chloride |

TABLE 1-continued

| Formula* | IUPAC** and Common Names | Chloride |
|---|---|---|
| X—(CH$_2$)$_8$—X | decanedioic (sebacic) acid | sebacyl chloride |

*X represents - COOH, and the balance of the formula defines an aliphatic moiety common to the acid and corresponding acid chloride.
**nomenclature adopted by The Council of the International Union of Pure and Applied Chemistry.

The compounds which are preserved by the technique taught in this application are succinyl chloride, glutaryl chloride, adipyl chloride, pimelyl chloride, suberyl chloride, azelayl chloride, and sebacyl chloride. Any one of these diacid chlorides may be preserved by allowing it to stand over a minor amount of one of the following: succinic acid, glutaric acid, adipic acid, pimelic acid, suberic acid, azelaic acid, or sebacic acid. If the carboxylic acid is added to the diacid chloride when the latter is already aged and discolored, the rate of clarification of the diacid chloride has been found to depend on the level of addition of the dicarboxylic acid.

As indicated in the Disclosure of Invention, the dicarboxylic acid chlorides forming the subject matter of the present invention may also be preserved or clarified by adding a small amount of water to the chloride. The water reacts with the dicarboxylic acid chloride as follows:

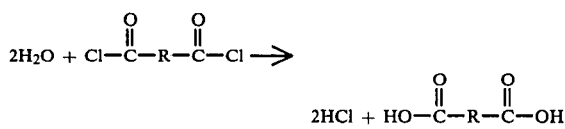

where R is an ethyl, propyl, butyl, pentyl, hexyl, heptyl or octyl moiety. The reaction proceeds essentially to completion so no water remains in the finished product, although HCl is a side product which may be undesirable in some applications. Sufficient water is added so that the weight of dicarboxylic acid in the product mixture is at least about 2% of the weight of the dicarboxylic acid chloride, preferably between 2% and 20% of the weight of the composition, or most preferably about 2% to 5% of the weight of the composition. One way to add water to the dicarboxylic acid chloride is to pass moist air through the chloride. However, this method of preserving the acid chloride is less preferred in commercial applications because a relatively expensive diacid chloride is thereby converted into a relatively inexpensive dicarboxylic acid.

When the dicarboxylic acid chlorides of this invention are clarified or preserved according to the teachings herein, the resulting chlorides may desirably be stored over the added dicarboxylic acid in order to prevent discoloration of the chloride during storage. When one desires to use the chloride thus stored in an application which requires removal of the dicarboxylic acid and any precipitate of discolored material which may be present due to the occurrence of the clarification reaction, the removal of the dicarboxylic acid and precipitate may be effected by any of the numerous means known to those skilled in the art. For example, the mixture may be filtered through any suitable filtering medium, or the chloride may be decanted from the solids residing in the storage vessel.

The amount of clarification resulting from the practice of the present invention may be measured using a Beckman Model 25 spectrophotometer, available from Beckman Instruments, Inc., 2500 Harbor Blvd., Fullerton, Calif. 92634, set at a wave length of 450 nanometers. The instrument is zeroed using chloroform in both the reference cell and the sample cell. When the measurements are made the reference cell contains chloroform, and the sample cell contains an undiluted sample of the preserved diacid chloride. The raw intensity reading and the reference intensity may be converted to optical adsorbency readings according to the following formula:

$$A = -\log(I/I_o)$$

where A is optical absorbency, I is intensity of light transmitted through the sample, and $I_o$ is the chloroform reference intensity.

In order to more completely illustrate the invention the following examples are provided. Each example is practiced at ambient temperature and pressure in an open reaction vessel. The dicarboxylic acids of this invention are all solids at room temperature and the acid chlorides are all liquids at room temperature, so the invention is practiced by adding a powdered solid dicarboxylic acid to a sample of the liquid acid chloride and allowing the former acid to drop to the bottom of the reaction vessel.

EXAMPLE 1

A sample of aged adipyl chloride, which before the test was dark brown, was stored in a glass reaction vessel over 2 percent by weight of the composition of powdered adipic acid at ambient temperature and pressure. Several days later the chloride was observed to be very clear. The resulting clarified chloride is decanted to separate it from the acid and products of discoloration.

EXAMPLE 2

The process of Example 1 is repeated, except that succinic acid is used as a preservative. The adipyl chloride is observed to be clarified as a result of this treatment, and the chloride is separated from the succinic acid by decanting it from the reaction vessel.

EXAMPLE 3

The process of Example 2 is repeated, except that glutaric acid is used as a preservative. The same result is noted.

EXAMPLE 4

The process of Example 2 is repeated except that pimelic acid is used as a preservative. The same result is noted.

EXAMPLE 5

The process of Example 2 is repeated, except that suberic acid is used as a preservative. The same result is noted.

EXAMPLE 6

The process of Example 2 is repeated, except that azelaic acid is used as a preservative. The same result is noted.

EXAMPLE 7

The process of Example 2 is repeated, except that sebacic acid is used as a preservative. The same result is noted.

EXAMPLE 8

The process of Example 1 was repeated, except that about 16.6 percent by weight of the composition of glutaric acid was used in the place of the adipic acid. After one day the chloride was pale yellow, and on the following day the pale yellow color remained.

EXAMPLE 9

The process of Example 1 was repeated, with the exception that 16.6 percent by weight of the composition of succinic acid was used as the preservative. In this case clarification was not complete, although after one day the chloride did turn lighter in color.

EXAMPLE 10

In this example, the procedure of Example 9 was followed with the exception that about 16.6 percent by weight of adipic acid was stored with the adipyl chloride. One day later the chloride appeared amber, and two days after the experiment was begun the adipyl chloride was water white.

EXAMPLE 11

The procedure of Example 9 was followed, with the exception that sebacic acid was used in place of succinic acid. One day after the addition of sebabic acid the chloride was pale yellow, and on the second day following the addition of sebacic acid the chloride was water white.

EXAMPLE 12

In this example adipyl chloride was preserved by partially hydrolyzing the chloride to form adipic acid which then performed the clarifying and stabilizing functions described in this specification. A quantity of discolored adipyl chloride was treated overnight in an open glass reaction vessel at ambient temperature and pressure by impinging a jet of nitrogen gas into the surface of the adipyl chloride. The jet caused some entrained air to enter the body of adipyl chloride, where an unknown amount of the water vapor typically found in air was hydrolyzed to form adipic acid. The next day the discoloration in the adipyl chloride was found to have settled out.

CONTROL

A sample of discolored adipyl chloride was allowed to stand in a glass reaction vessel for two days as a control. No change in the color of this sample was observed.

Spectrophotometric Data

Table 2 summarizes several of the examples and the control, and provides the optical absorbency of each sample after being allowed to stand for two days.

TABLE 2

| Example | Acid | Chloride | Parts by Wt. Acid | Parts by Wt. Chloride | Optical Absorbency |
|---------|------|----------|-------------------|-----------------------|--------------------|
| 1 | adipic | adipyl | 1 | 49 | — |
| 8 | glutaric | adipyl | 1 | 5 | 0.245 |
| 9 | succinic | adipyl | 1 | 5 | 0.321 |
| 10 | adipic | adipyl | 1 | 5 | 0.393 |
| 11 | sebacic | adipyl | 1 | 5 | 0.109 |
| Control | — | adipyl | — | 5 | 1.73 |

After about two months, several of the samples produced for the above examples became colored, but these colored samples did not contain the opaque particulate matter found in untreated portions of the dicarboxylic acid chlorides.

The clarified products of Examples 1–6 have utility as raw materials for the manufacture of certain polyester foam materials in accordance with the teaching of U.S. patent application, Ser. No. 843,606, cited supra at page 2. When the clarified dicarboxylic acid chlorides are to be used in this way, the dicarboxylic acid chlorides are removed from the precipitated discolored matter and residual dicarboxylic acid solids immediately before using the chlorides in polymerization reactions.

What is claimed is:

1. A method to separate an aliphatic dicarboxylic acid chloride from its discolored products of aging, comprising the steps of:
   (a) Providing a quantity of a dicarboxylic acid chloride, having the formula

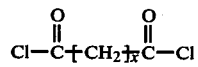

where x is an integer between 2 and 8 inclusive, which contains discolored products of aging;
   (b) Contacting therewith at least about 2 percent by weight of the composition of a dicarboxylic acid, having the formula

where y is an integer between 2 and 8 inclusive, to precipitate said discolored products of aging, producing a clarified dicarboxylic acid chloride; and
   (c) Separating said clarified dicarboxylic acid chloride from said discolored products of aging and said dicarboxylic acid.

2. The method of claim 1, wherein said contacting step is performed by adding to said dicarboxylic acid chloride a quantity of water effective to hydrolyze said dicarboxylic acid chloride to form at least about 2 percent by weight of the composition of the corresponding dicarboxylic acid.

3. The method of claim 1, wherein said dicarboxylic acid comprises 2 to 20 percent by weight of the composition.

4. The method of claim 3, wherein said dicarboxylic acid comprises 2 to 5 percent by weight of the composition.

5. The method of claim 1, wherein the value of x is 4.

6. The method of claim 3, wherein the value of y is 4.

7. A method to prevent discoloration upon standing of a dicarboxylic acid chloride, having the formula

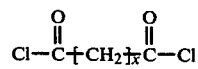

where x is an integer between 2 and 8 inclusive, comprising the step of storing said dicarboxylic acid chloride in contact with at least about 2 percent by weight of the composition of a dicarboxylic acid having the formula

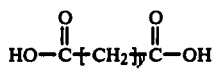

where y is an integer between 2 and 8 inclusive.

8. The method of claim 7, wherein said dicarboxylic acid comprises 2 to 20 percent by weight of the composition.

9. The method of claim 8, wherein said dicarboxylic acid comprises 2 to 5 percent by weight of the composition.

10. The method of claim 7, wherein x has the value 4.

11. The method of claim 10, wherein y has the value 4.

12. A stabilized dicarboxylic acid chloride composition comprising a major amount of a dicarboxylic acid chloride, having the formula

where x is an integer between 2 and 8 inclusive, stored in contact with at least about 2 percent by weight of the composition of a carboxylic acid having the formula

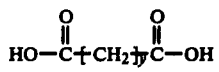

where y is an integer between 2 and 8 inclusive.

13. The composition of claim 12 wherein said dicarboxylic acid comprises 2 to 20 percent by weight of the composition.

14. The composition of claim 13 wherein the dicarboxylic acid comprises about 2 to 5 percent by weight of the composition.

* * * * *